US008211681B2

(12) United States Patent
Zhang et al.

(10) Patent No.: US 8,211,681 B2
(45) Date of Patent: Jul. 3, 2012

(54) BIOHYDROGEN PRODUCTION BY AN ARTIFICIAL ENZYMATIC PATHWAY

(75) Inventors: Yi-Heng Percival Zhang, Blacksburg, VA (US); Jonathan Mielenz, Knoxville, TN (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 433 days.

(21) Appl. No.: 11/747,496

(22) Filed: May 11, 2007

(65) Prior Publication Data
US 2007/0264534 A1 Nov. 15, 2007

Related U.S. Application Data

(60) Provisional application No. 60/799,685, filed on May 12, 2006.

(51) Int. Cl.
*C12P 5/00* (2006.01)
*C12P 3/00* (2006.01)
*C01B 3/02* (2006.01)
*H01M 8/16* (2006.01)

(52) U.S. Cl. ..................... 435/166; 435/168; 423/648.1; 429/2

(58) Field of Classification Search .................. 435/166, 435/168; 423/648.1; 429/2
See application file for complete search history.

(56) References Cited

U.S. PATENT DOCUMENTS

| 5,942,424 | A | 8/1999 | Woodward | |
|---|---|---|---|---|
| 6,846,584 | B2 * | 1/2005 | Dutil et al. | 429/19 |
| 7,393,669 | B2 * | 7/2008 | Bro et al. | 435/139 |
| 2005/0009135 | A1 | 1/2005 | Bro et al. | |

OTHER PUBLICATIONS

Woodward, et al, "Efficient Production of Hydrogen from Glucose-6-Phosphate" May 2000, U.S. DOE Hydrogen Program Annual Review Meeting pp. 1-9.*
Bae et al "Facile synthesis of glucose-1-phosphate from starch by *Thermus caldophilus* GK24 alpha-glucan phosphorylase" 2005 "Process Biochemistry" vol. 40 pp. 3707-3713.*
Extended European Search Report and Written Opinion, Application No. 07783690.6, Issued May 17, 2010.
Hallenbeck, P.C., et al., "Biological hydrogen production; fundamentals and limiting processes," Intl. J. of Hydrogen Energy, Elsevier Science Publishers B.V., Barking, GB, vol. 27, No. 11-12, pp. 1185-1193 (Nov. 1, 2002).
Woodward, J, et al., "In Vitro Hydrogen Production by Glucose Dehydrogenase and Hydrogenase," Tio/Technology, Nature Publishing Co., New York, US, vol. 14, No. 7, pp. 872-874 (Jul. 1, 1996).
Woodward, Jonathan, et al., "Enzymatic conversion of sucrose to hydrogen," Biotechnology Progress, vol. 14, No. 6, pp. 897-902 (Nov. 6, 1998).
Alper J., Science 2003, 299:1686-1687.
Benemann et al., Proc. Nat. Acad. Sci. USA 70:2317, 1973.
Bryant F.O. and Adams M.W.W, J. Biol. Chem. 1989, 264:5070-5079.
Co-pending application in Europe No. 07783690, file history as of Jan. 20, 2012.
Co-pending China Application No. 200780026279.9, Office Action dated Jul. 28, 2011and translation.
Cortright R.D. et al., Nature 2002, 418:964-967.
Deluga G.A. et al., Science 2004, 303:993-997.
Farrell A.E. et al., Science 2006, 311:506-508.
Hoffert M.I. et al., Science 2002, 298:981-987.
Huber G.W. et al., Science 2003, 300:2075-2077.
Klein and Betz, Plant Physiol. 61:953, 1978.
Lynd L.R. et al., Microbiol. Mol. Biol. Rev. 2002, 66:506-577.
Lynd, L.R., et al., "Consolidated bioprocessing of cellulosic biomass: An update," 2005 Curr. Opin. Biotechnol. 16:577-583.
Ma K. and Adams M.W., J. Bacteriol. 1994, 176:6509-6517.
Ma K. et al., J. Bacteriol. 2000, 182:1864-1871.
Ma, et al., "Hydrogen production from pyruvate by enzymes purified from the hyperthermophilic archaeon, *Pyrococcus furiosus*: A key role for NADPH," FEMS Microbiol. Lett. (1994) 122: 245-250.
Markov et al., "The Potential of Using Cyanobacteria in Photobioreactors for Hydrogen Production," Advances in Biochemical Engineering and Biotechnology 52:60-86, 1995.
Morris D., J. Sci. Food Agric. 86:1743-1746 (2006).
Muir M. et al., J. Bacteriol. 1985, 163:1237-1242.
Pedroni, et al., "Characterization of the locus encoding the [Ni-Fe] sulfhydrogenase from the archaeon *Pyrococcus furiosus*: evidence for a relationship to bacterial sulfite reductases," Microbiol. 1995, 141:449-458.
Rao et al., "Hydrogen evolution by chloroplast-hydrogenase systems : improvements and additional observations," Biochimie 60:291-296, 1978.
Rosen, M. M. and Krasna, A. I. (1980), Limiting Reactions in Hydrogen Photoproduction by Chloroplasts and Hydrogenase. Photochemistry and Photobiology, 31: 259-265.
Vatsala and Seshadri, "Microbial Production of Hydrogen—A Review," Proc. Indian Nat'l Sci. Acad, 1985, B51:282-295.
Woodward, J., "Enzymatic production of biohydrogen," Nature vol. 405, Jun. 29, 2000, pp. 1014-1015.
Zhang Y.-H.P. and Lynd L.R., Appl. Environ. Microbiol. 2004, 70:1563-1569.
Zhang Y.-H.P. and Lynd L.R., Appl. Microbiol. Biotechnol. 2006, 70:123-129.
Zhang Y.-H.P. and Lynd L.R., Proc. Natl. Acad. Sci. USA 2005, 102:7321-7325.

* cited by examiner

*Primary Examiner* — Herbert J Lilling
(74) *Attorney, Agent, or Firm* — New River Valley IP Law; Michele L. Mayberry

(57) ABSTRACT

The present invention comprises an in vitro enzymatic process that effectively converts renewable polysaccharides into high yields of hydrogen at mild conditions, using only enzymes and water. The process comprises a number of enzymes: (1) phosphorylases, (2) phosphoglucomutases, (3) hydrogenases, and (4) enzymes involved in the pentose-phosphate pathway. Preferred embodiments of the process produce only hydrogen and carbon dioxide as net products, translating into an inexpensive method of generating hydrogen in very large quantities from low-cost feedstocks.

20 Claims, 3 Drawing Sheets

BIOHYDROGEN PRODUCTION BY AN ARTIFICIAL ENZYMATIC PATHWAY

CROSS-REFERENCE TO RELATED APPLICATIONS

This application relies on the disclosure of and claims priority to U.S. Provisional Patent Application No. 60/799,685, filed May 12, 2006, the entire disclosure of which is hereby incorporated herein by reference.

GOVERNMENT CONTRACT

The United States Government has rights in this invention pursuant to Contract No. DE-AC05-00OR22725 between the United States Department of Energy and UT-Battelle, LLC.

BACKGROUND OF THE INVENTION

1. Field of the Invention

The present invention relates to biotechnology in the fields of agriculture and energy production. More specifically, the present invention relates to the production of hydrogen from renewable polysaccharides through enzymatic catalysis of polysaccharides substantially into hydrogen and carbon dioxide.

2. Discussion of Related Art

Climate change and the eventual depletion of the world's fossil-fuel reserves are threatening sustainable development (Morris, 2006; Hoffert et al., 2002; Farrell et al., 2006). Hydrogen is a mobile energy carrier and is abundant, clean, and of course does not contain carbon. According to the United States Department of Energy (2004), R&D priorities for the future hydrogen economy include (i) decreasing hydrogen production costs, (ii) finding viable methods for high-density hydrogen storage, (iii) establishing a safe and effective infrastructure for seamless delivery of hydrogen from production to storage to use, and (iv) dramatically lowering the costs of fuel cells and improving their durability.

Hydrogen is a very promising alternative for storing energy rather than employing fossil fuels. Hydrogen can be utilized in a fuel cell, which is an electrochemical device that converts the chemical energy of a reaction directly into electrical energy. A fuel cell is a highly efficient device for generating power and heat. Fuel cells offer the potential to significantly decrease reliance on fossil fuels. However, fuel supply is one of the major obstacles preventing widespread commercialization of such devices.

Most fuel cells operate by using hydrogen gas as the reactant, generally made by reforming (converting) a hydrogen compound. Hydrogen-rich fossil fuels are most commonly reformed using catalytic steam reforming, auto-thermal reforming, or catalytic partial-oxidation reforming. For fuel-cell technology to sustain our energy needs, though, renewable sources of hydrogen are required. Examples of non-fossil-fuel based hydrogen generation include electrolysis of water using solar or wind power, hydropower, or geothermal energy; thermochemical water splitting; waste gases at industrial sites; gasification of biomass; and bio- or photobiological systems that produce hydrogen gas upon digesting organic components or upon absorption of sunlight.

Unlike electricity, which must be used as it is produced, hydrogen can be stored until needed. The low density of hydrogen, however, translates into a low energy density, particularly in comparison with traditional fuels. Even factoring into account the higher efficiency of a fuel cell compared with traditional power-generation methods, the low energy density of hydrogen dictates potentially inhibitive storage and transportation methods.

Polysaccharides can be a good means of storage for hydrogen because polysaccharides contain about 6.2% by mass $H_2$ per sugar unit, and when it reacts with water, it can produce 12 moles of dihydrogen. So the potential hydrogen storage capacity is around 15%. A material with 15% hydrogen storage capacity exceeds even long-term objectives for hydrogen-storage technologies, according to U.S. Department of Energy goals (Schlapbach and Zuttel, 2001). In order to actually extract hydrogen from polysaccharides and water, the overall reaction $C_6H_{10}O_5 + 7 H_2O \rightarrow 6 CO_2 + 12 H_2$ needs to take place, where $C_6H_{10}O_5$ represents glucan repeat units contained in biomass, such as starch or cellulose.

There have been several paradigms for converting biomass to hydrogen: (1) direct polysaccharide gasification (Antal et al., 2000); (2) direct glucose chemical catalysis (Cortright et al., 2002; Huber et al., 2003); (3) anaerobic fermentation (Das and Veziroglu, 2001; Hallenbeck and Benemann, 2002); and (4) ethanol fermentation (Lynd et al., 2002; Zhang et al., 2006; Zhang and Lynd, 2004) followed by ethanol reforming (Deluga et al., 2004). The conventional chemical methods have low hydrogen yields (<60%) and require high reaction temperatures (e.g., 500-900 K) (Antal et al., 2000; Cortright et al., 2002; Huber et al., 2003). Anaerobic hydrogen fermentation is well known for low efficiency with a maximum yield of 33% (Das and Veziroglu, 2001; Hallenbeck and Benemann, 2002). The combination of ethanol fermentation and reformation can produce 10 $H_2$ per glucose unit (83% yield). Considering 5-10% fermentation loss and around 5% reforming loss (Deluga et al., 2004), the practical hydrogen yield through ethanol could be approximately 75% of the maximum yield (the maximum yield being 12 $H_2$ per glucose unit).

Storage and distribution of solid polysaccharides to be converted to hydrogen could address many challenges of the hydrogen art today. If a practical process and apparatus could be used directly on board mobile applications, such as vehicles, several problems associated with hydrogen-storage devices could be solved. Namely, energy loss for hydrogen compression or liquefaction would be avoided. Additionally, high temperatures for $H_2$ desorption would no longer be necessary. Furthermore, solid hydrogen storage materials lifetime and hydrogen refilling time are not problems to practical applications any more. Also, storage and distribution of carbohydrate is very safe as compared to gaseous hydrogen.

The biochemical pathway for molecular hydrogen production from elemental hydrogen is known. An electron on photosystem I (either isolated photosystem I or photosystem I in thylakoids) is excited, typically by light, to a higher energy, resulting in the donation of an electron to an exogenous electron carrier that in turn can transfer electrons to the enzyme hydrogenase. In this process, oxidized photosystem I can then extract an electron from an electron donor, either directly or through an electron transfer chain, such as that found in the thylakoid membrane. Where water acts as the electron donor, the electron transfer chain includes photosystem II. Meanwhile, two reduced electron carrier molecules are able to donate electrons to the enzyme hydrogenase. Hydrogenase combines two electrons with two protons to form a hydrogen molecule.

Aerobic oxygen-producing photosynthetic organisms, or subcellular components from such organisms, have been used previously to make hydrogen gas (Benemann et al., 1973; Rosen and Krasna, 1980; Rao et al., 1978). The components of cell-free (i.e., in vitro) systems reported in these references require isolated thylakoids or solubilized photosystem I from thylakoids; an electron donor, such as water or an artificial electron donor such as dithiothreitol or ascorbic acid; a hydrogenase capable of accepting electrons from photosystem I that can catalyze the combination of two electrons and two protons to form molecular hydrogen when electrons are received from an electron donor that can be oxidized by the hydrogenase; and an exogenous electron carrier that is capable of accepting electrons from photosystem I and can donate electrons to the hydrogenase.

At least two groups of oxygen-producing photosynthetic organisms are capable of producing hydrogen in vivo. These include cyanobacteria and green algae. Cyanobacteria generally use the enzyme nitrogenase to produce molecular hydrogen. Electrons used in this molecular hydrogen-producing process are derived from stored carbohydrate and are used to reduce ferredoxin, which is the immediate electron donor for nitrogenase (Markov et al., 1995). Hydrogenase can also catalyze molecular hydrogen production in cyanobacteria. In cyanobacteria, molecular hydrogen production is inhibited by oxygen and/or light.

Green algae can also photoevolve (i.e., produce) molecular hydrogen via hydrogenase. The pathway of electron transfer is currently unknown. The source of electrons for the process has been shown to be endogenously fermented carbohydrate (Klein and Betz, 1978). Hydrogen production stops in the presence of carbon dioxide (Vatsala and Seshadri, 1985), indicating that the electron sink of carbon dioxide reduction is a better competitor for photosynthetic electron flow than hydrogenase.

Molecular hydrogen ($H_2$) has a number of commercial uses. Molecular hydrogen is used for the production of ammonia; in petroleum refining, where $H_2$ is used throughout a typical refinery; in the chemical-synthesis industries, when conversion of a double carbon-carbon bond to a single C—C bond is desired, or of a triple carbon-carbon bond to a single or double bond; in the food industry for hydrogenation of vegetable oils; and in electronic-circuitry manufacture. Hydrogen is also used extensively today to make methanol, fertilizers, glass, refined metals, vitamins, cosmetics, soaps, lubricants, and cleaners. Further, pure hydrogen is an excellent fuel, both in traditional combustion engines as well as in fuel cells, and produces only water vapor when oxidized with oxygen. Liquid hydrogen can also be used as a fuel, such as in space vehicles.

The state of the art for hydrogen fuel generation today has many challenges, such as limited yield, high energy input required, high costs, and additional purification steps to ensure that the fuel is sufficiently clean. What is needed is an inexpensive method of generating hydrogen in very large quantities, sufficient to support extensive use of fuel cells and other uses of hydrogen. Especially desirable are practical processes, compositions, kits, and apparatus to convert renewable feedstocks, such as abundant biomass containing polysaccharides, directly into hydrogen. It is desired that the process is capable of high yields to $H_2$ and of good mass and energy efficiency, and ultimately of low cost.

SUMMARY OF THE INVENTION

The present invention provides methods, compositions, and kits for generation of hydrogen from biomass. The hydrogen so produced can be used for any number of things, and is well suited for use as a fuel for production of energy. The present invention is based, at least in part, on integrated network of enzymatic reactions that can convert glucan units from polysaccharides plus water to hydrogen and carbon dioxide:

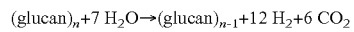
$$(glucan)_n + 7\,H_2O \rightarrow (glucan)_{n-1} + 12\,H_2 + 6\,CO_2$$

where (glucan) is an anhydroglucose unit, —$C_6H_{10}O_5$—. The hydrogen comes from polysaccharides and water. In essence, the present invention relies on the energy stored in polysaccharides to break up water and produce hydrogen. Polysaccharides can include (but are not limited to) starch, cellulose, hemicellulose, maltose, isomaltose, cellobiose, β-1,4-glucan, β-1,3-glucan, β-1,6-glucan, α-1,4-glucan, α-1,6-glucan, or any other oligomers of monomeric sugar units linked by glycosidic bonds.

In a first aspect, the invention provides a process or method for producing hydrogen from a polysaccharide. In general, the process comprises: reducing the length of the polysaccharide by converting at least a portion of it to glucose-6-phosphate; and generating hydrogen from the glucose-6-phosphate. The process may be carried out through a number of specific chemical and enzymatic steps.

For example, the process of reducing the length of the polysaccharide may comprise phosphorylating a terminal glucan unit of the polysaccharide, resulting in cleavage and release of the terminal unit from the polysaccharide from which it originated. Such a phosphorylation can be accomplished by any number of phosphorylases, which can couple cleavage of a glycosidic bond in polysaccharide to incorporation of a phosphate group into a released glucan unit to form glucose-6-phosphate. The process does not use ATP or other high energy phosphate-bond compounds.

In addition, production of glucose-6-phosphate may be accomplished by any suitable means. Preferably, the glucan unit released from the polysaccharide is a glucose-6-phosphate unit. However, more typically, when enzymatic reactions are used, it will be a glucose-1-phosphate unit, which must be isomerized to a glucose-6-phosphate unit. Isomerization may be accomplished by any suitable chemical or enzymatic process. Enzymatic conversion is preferred.

Hydrogen production from glucose-6-phosphate can likewise be accomplished by any suitable chemical or biochemical means. According to preferred embodiments, the glucose-6-phosphate is converted to hydrogen by way of an enzymatic process that involves conversion of the glucose-6-phosphate to ribulose-5-phosphate, typically by way of 6-phosphogluconate (6PG). According to an exemplary embodiment, conversion of 6 moles of glucose-6-phosphate to 6 moles of ribulose-5-phosphate yields 12 moles of molecular hydrogen.

It is well understood that reactions, whether they be chemical or biochemical, have equilibria and net product ceases to be formed once the equilibrium for a particular reaction is reached. To facilitate and maximize production of hydrogen in the present process, ribulose-5-phosphate is removed from the reaction equation by conversion of the ribulose-5-phosphate to various products. According to the invention, the product(s) can vary widely, the goal being to drive the reaction toward use of the ribulose-5-phosphate to allow continued production of hydrogen. A convenient way to decrease the amount of ribulose-5-phosphate in the system is to remove it by way of some or all of the enzymatic steps of the pentose phosphate pathway, which is well-known and widely understood in the art.

As should be evident, where the process involves enzymatic production of hydrogen, the process includes use of a hydrogenase. The hydrogen produced by the process may be released to the atmosphere, but is preferably collected and either immediately used or stored for later use as a fuel source. For example, the process may comprise at least partial separation of the hydrogen from carbon dioxide present in the reaction vessel. In addition, some or all of the hydrogen can be fed into a fuel cell for electricity generation or other energy production.

Thus, in an exemplary embodiment, the process can comprise: (a) providing a composition (e.g., mixture) comprising at least one polysaccharide and water; (b) providing one or more enzymes with phosphorylase activity; (c) phosphorylating at least some of the polysaccharide to reduce the chain length of the polysaccharide and produce glucose-1-phosphate; (d) providing one or more enzymes with phosphoglucomutase activity; (e) isomerizing at least some of the glucose-1-phosphate produced in step (c) into glucose-6-phosphate; (f) providing a plurality of enzymes effective to catalyze the steps of the pentose phosphate pathway; (g) providing one or more enzymes with hydrogenase activity; and (h) forming hydrogen from at least some of the glucose-6-phosphate produced in step (e).

The process of the invention, in its general, basic form or as described in detailed embodiments, can be performed in any convenient manner. Thus, all of the chemical or biochemical reaction steps may be performed in a single reaction vessel. Alternatively, one or some of the reactions may be performed separately. The process may be performed as a batch process or as a continuous process, with hydrogen and waste products being removed continuously and new raw materials being introduced.

In embodiments, at least one of the enzymes for phosphorylating the polysaccharide is a phosphorylase, such as 1,4-α-glucan phosphorylase, α-glucan phosphorylase, amylopectin phosphorylase, amylophosphorylase, glucan phosphorylase, glucosan phosphorylase, glycogen phosphorylase, maltodextrin phosphorylase, maltose phosphorylase, cellobiose phosphorylase, cellodextrin phosphorylase, and sucrose phosphorylase. In certain embodiments, at least one of the enzymes for production of hydrogen is a hydrogenase from the archaebacterium *Pyrococcus furiosus*.

Optionally, inorganic phosphate can be added to the process in an amount that is in excess of the inorganic phosphate otherwise generated in the process. In preferred embodiments, phosphate does not accumulate in the system. Also, preferably, ATP is not generated or consumed during the process.

Where the process of the invention comprises enzymatic reactions, the process can also be characterized be reference to the following enzymatic functionalities: (a) phosphorylating at least some of the polysaccharide to produce glucose-1-phosphate; (b) isomerizing at least some of the glucose-1-phosphate into glucose-6-phosphate; and (c) forming hydrogen from at least some of the glucose-6-phosphate.

Advantageously, the process can be conducted at low to moderate temperatures, such as between 10° C. and 100° C. In some embodiments, no external chemical energy source is added (other than polysaccharide), and the only energy added to the system is heat. That is, in general, the overall reaction is a weakly endothermic reaction, and thus needs small amounts of heat input. For example, the heat energy added could be obtained from fuel cells. Preferably, the system is maintained at a constant temperature, taking into consideration that the temperature is a function of substrate concentrations, net heats of reactions, and heat losses in the particular system. In embodiments, the process comprises heating the reaction to between about 10° C. and about 100° C.

According to the present invention, the process yield of hydrogen is typically at least 10 moles of hydrogen per mole of anhydroglucose units contained in the starting polysaccharide. In preferred embodiments, the yield of hydrogen is about or at least 11, about or at least 11.5, about or at least 11.6, about or at least 11.7, about or at least 11.8, or about or at least 11.9 moles of hydrogen per mole of anhydroglucose units contained in the starting polysaccharide. In especially preferred embodiments, the yield of hydrogen is 12 moles $H_2$ per mole anhydroglucose units in the polysaccharide, corresponding to 100% of theoretical yield.

The maximum rate of hydrogen production during the process of the invention is not limited. However, it is preferably at least 0.1, at least 0.2, at least 0.4, at least 0.6, at least 0.8, or at least 1.0 (or higher) mmol/L/hr.

In an additional aspect, the invention provides compositions that are effective for generating hydrogen in vitro from a polysaccharide. In general, the compositions comprise: (a) at least one polysaccharide; (b) water; (c) at least one enzyme that is capable of catalyzing the conversion of the polysaccharide(s) to glucose-6-phosphate, conversion of glucose-6-phosphate to 6-phosphogluconate, and conversion of 6-phosphogluconate to ribulose-5-phosphate; (d) at least one enzyme that is capable of converting $NADP^+$ and glucose-6-phosphate and/or $NADP^+$ and 6-phosphogluconate to NADPH and protons; and (e) at least one enzyme that is capable of catalyzing the conversion of NADPH and protons to hydrogen. In preferred embodiments, the composition also comprises a plurality of enzymes capable of catalyzing some or all of the steps of the pentose phosphate pathway.

In certain embodiments, the compositions include the following enzymes (as characterized by EC numbers): (i) an enzyme that is at least 80%, preferably at least 90%, more preferably at least 95% identical to EC 2.4.1.1; (ii) an enzyme that is at least 80%, preferably at least 90%, more preferably at least 95% identical to EC 5.4.2.2; (iii) an enzyme that is at least 80%, preferably at least 90%, more preferably at least 95% identical to EC 1.1.1.49; (iv) an enzyme that is at least 80%, preferably at least 90%, more preferably at least 95% identical to EC 1.1.1.44; (v) an enzyme that is at least 80%, preferably at least 90%, more preferably at least 95% identical to EC 5.3.1.6; (vi) an enzyme that is at least 80%, preferably at least 90%, more preferably at least 95% identical to EC 5.1.3.1; (vii) an enzyme that is at least 80%, preferably at least 90%, more preferably at least 95% identical to EC 2.2.1.1; (viii) an enzyme that is at least 80%, preferably at least 90%, more preferably at least 95% identical to EC 2.2.1.2; (ix) an enzyme that is at least 80%, preferably at least 90%, more preferably at least 95% identical to EC 5.3.1.1; (x) an enzyme that is at least 80%, preferably at least 90%, more preferably at least 95% identical to EC 4.1.2.13; (xi) an enzyme that is at least 80%, preferably at least 90%, more preferably at least 95% identical to EC 3.1.3.11; (xii) an enzyme that is at least 80%, preferably at least 90%, more preferably at least 95% identical to EC 5.3.1.9; and (xiii) an enzyme that is at least 80%, preferably at least 90%, more preferably at least 95% identical to EC 1.12.1.3. In preferred process and composition embodiments, there are no hydrolytic enzymes present.

In another aspect, the invention provides kits for producing hydrogen from one or more polysaccharides. In general, a kit of the invention comprises one or more containers, each independently containing one or more of: (a) one or more enzymes capable of phosphorylating glucan units of a polysaccharide; (b) one or more enzymes capable of isomerizing glucose-1-phosphate to glucose-6-phosphate; (c) one or more enzymes capable of producing molecular hydrogen from oxidation of glucose-6-phosphate, 6-phosphogluconate, or both. In embodiments, the kits comprise glucose-6-phosphate dehydrogenase, 6-phosphogluconate dehydrogenase, or both. In embodiments, the kits comprise one or more phosphorylases, one or more phosphoglucomutases, and one or more hydrogenases. The kits of the invention can also contain an enzyme composition as described above.

The kits of the invention can also provide some or all of the supplies needed to perform a method of the invention (i.e., produce hydrogen from biomass). It thus may contain enzymes, buffers, solvents, containers (e.g., one or more containers for collecting or using some or all of the hydrogen gas that evolves from the reaction process and system of the invention).

DETAILED DESCRIPTION OF EMBODIMENTS OF THE INVENTION

Figure 1:
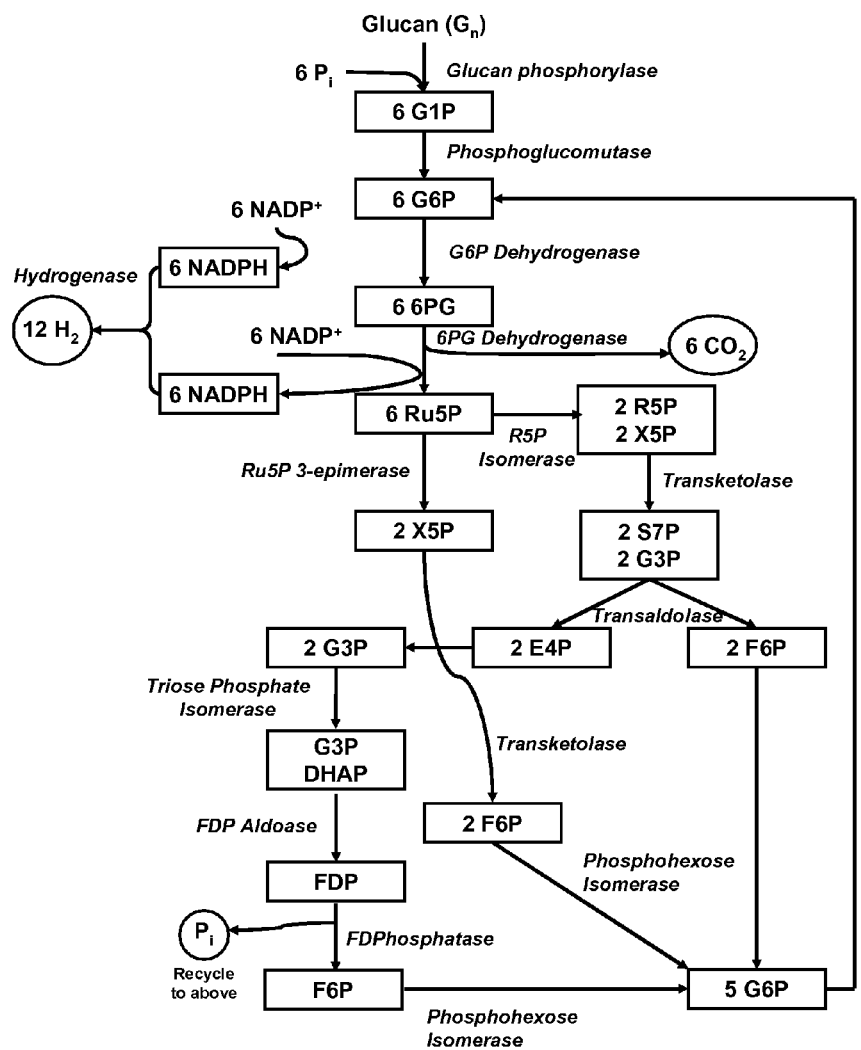
FIG. 1 depicts a synthetic metabolic pathway for the conversion of a polysaccharide and water into hydrogen and carbon dioxide according to the present invention.

The following description provides a detailed discussion of certain embodiments and features of the systems, processes, compositions, and kits of the invention. It is not meant to be exhaustive of all such embodiments and features, but rather is presented to give the reader a better understanding of selected exemplary embodiments and features.

To give the reader a better understanding of the invention, certain terms are now defined and/or discussed. Terms not discussed or defined herein are to be understood as being used in their normal and customary way in the art.

By "polysaccharide" it is meant any oligomer or polymer of glucan units larger than monomers. Polysaccharide will thus be used interchangeably with "oligosaccharide", "glucan", "sugar oligomer", and "sugar polymer". Polysaccharides can include (but are not limited to) starch, cellulose, hemicellulose, pectin, maltose, isomaltose, cellobiose, β-1,4-glucan, β-1,3-glucan, β-1,6-glucan, α-1,4-glucan, α-1,6-glucan, or any other oligomers of monomeric sugar units linked by glycosidic bonds. Mixtures of any number of polysaccharides can also be used, and such mixtures are included in the term "polysaccharides".

As used herein, "enzymes" are protein catalysts that catalyze (i.e., accelerate) chemical and biochemical reactions. As used herein, "enzyme" is meant to encompass a single enzyme, mixtures comprising one or more enzymes, or enzyme complexes. As used herein, "enzyme unit" (or "unit") is defined as an amount of an enzyme that catalyzes the conversion of 1 micromole (um) of substrate per minute. The conditions for the purposes of the definition of enzyme unit are a temperature of 30° C. and the pH value and substrate concentration that yield the maximum substrate conversion rate.

The Enzyme Commission number (EC number) is a numerical classification scheme for enzymes, based on the chemical reactions they catalyze. For the purposes of the present invention, an EC number will also be used to specify enzymes. When an enzyme is characterized by an EC number herein, it is understood that there can be multiple enzymes from different sources or organisms that all catalyze the same reaction. The invention is not limited to any particular enzyme or source of enzymes, but rather to certain enzyme-catalyzed reactions in a pathway, as will be described below.

The language "an enzyme that is characterized by EC 2.4.1.11", for example, means any amino acid sequence that has the EC number 2.4.1.1 according to at least one art-recognized enzyme information system (such as BRENDA or KEGG) as of the filing date of this application.

As is known in the art, "identity" between two enzymes is determined by comparing the amino acid sequence of one enzyme to the sequence of a second enzyme. Identity may be determined by procedures which are well-known in the art, for example, by utilizing BLAST (Basic Local Alignment Search Tool at the National Center for Biological Information). When enzyme identity is recited in conjunction with an enzyme EC number, according to the present description it is to be understood that there can be many different amino acid sequences that all have the same EC number. Thus, for example, the language "an enzyme that is at least 90% identical to EC 2.4.11" means an amino acid sequence that is computed to have 90% or better sequence identity to at least one amino acid sequence that has the EC number 2.4.1.1 according to at least one art-recognized enzyme information system (such as BRENDA or KEGG) as of the filing date of the present application.

Unless otherwise indicated, all numbers expressing concentrations of components, reaction conditions, stoichiometries, and so forth used in the specification and claims are to be understood as being modified in all instances by the term "about", which indicates that the stated value encompasses all values above or below it by 5% of the value and/or within the level of error intrinsic to the method of obtaining the value. Accordingly, unless indicated to the contrary, the numerical parameters set forth in the following specification and attached claims are approximations that may vary depending at least upon the specific analytical technique. The numerical values set forth are reported as precisely as possible. Any numerical value, however, inherently contains certain errors necessarily resulting from the standard deviation found in their respective testing measurements.

In typical enzymatic practice of certain embodiments of the methods and use of embodiments of the systems, compositions, and kits of the invention, the present invention enzymatically converts polysaccharides, which can be represented by the glucan repeat unit —$C_6H_{10}O_5$—, into hydrogen and carbon dioxide through the following overall (net) reaction:

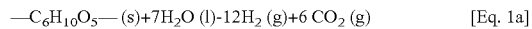
$$—C_6H_{10}O_5—(s)+7H_2O\,(l)\text{-}12H_2\,(g)+6\,CO_2\,(g) \qquad [\text{Eq. 1a}]$$

Note that 5 moles of $H_2$ are generated from a glucan repeat unit, while the other 7 moles of $H_2$ come from reacted water. The (s), (l), and (g) tags indicate that the chemical species is in the solid, liquid, and gas phase, respectively. It will be understood that polysaccharides will typically be suspended, substantially solubilized, or completely dissolved in the liquid phase, depending on the particular polysaccharides selected as well as temperature and other conditions.

FIG. 1 shows a synthetic enzymatic pathway comprised of 13 reversible enzymatic reactions: a) a chain-shortening phosphorylation reaction catalyzed by phosphorylase yielding glucose-1-phosphate (Eq. 2); b) the conversion of glucose-1-phosphate (G-1-P) to glucose-6-phosphate (G-6-P) catalyzed by phosphoglucomutase (Eq. 3); c) a pentose-phosphate pathway containing 10 enzymes (Eq. 4); and d) hydrogen generation from NADPH catalyzed by hydrogenase (Eq. 5).

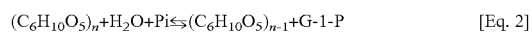
$$(C_6H_{10}O_5)_n+H_2O+Pi \rightleftharpoons (C_6H_{10}O_5)_{n-1}+G\text{-}1\text{-}P \qquad [\text{Eq. 2}]$$

$$G\text{-}1\text{-}P \rightleftharpoons G\text{-}6\text{-}P \qquad [\text{Eq. 3}]$$

$$G\text{-}6\text{-}P+12\,NADP^++6\,H_2O \rightleftharpoons 12\,NADPH+12\,H^++6\,CO_2+Pi \qquad [\text{Eq. 4}]$$

$$12\,NADPH+12\,H^+ \rightleftharpoons 12\,H_2+12\,NADP^+ \qquad [\text{Eq. 5}]$$

In embodiments, the enzymatic pathway of the invention comprises three main blocks: (a)(1) polysaccharide chain-shortening phosphorylation catalyzed by phosphorylases, followed by (a)(2) conversion from glucose-1-phosphate to glucose-6-phosphate catalyzed by phosphoglucomutase; (b) the pentose-phosphate pathway, comprising an oxidative phase, which converts G-6-P to ribulose-5-P, $CO_2$, and NADHP; and a non-oxidative phase, which can regenerate ribulose-5-P to G-6-P; and (c) hydrogen generation from NADPH catalyzed by hydrogenase.

The combination of chain-shortening by glucan phosphorylase and the conversion from G-1-P to G-6-P enables the utilization of the energy stored in glucosidic bonds of polysaccharides. In contrast, conventional hydrolysis of glucosidic bonds of polysaccharides dissipates such energy. Because the gaseous reaction products ($H_2$ and $CO_2$) can be removed from the liquid solution simultaneously, the reaction can be effectively driven forward towards hydrogen production, while the polysaccharide chains are being simultaneously shortened in concurrent reaction paths.

Generally, the overall reaction can be written as $$(glucan)_{n+a} \, H_2O \rightarrow (glucan)_{n-1+b} \, H_2 + c \, CO_2 \quad [Eq. 1b]$$

where the coefficient b defines the yield of hydrogen obtained from the starting polysaccharide. Thermodynamically, the reaction represented by Eq. 1 is a spontaneous process ($\Delta G O° = -48.9$ kJ/mol) and is an endothermic reaction ($\Delta H° = 595.6$ kJ/mol) (Atkins and De Paula, 2005). When the gaseous products ($H_2$ and $CO_2$) are continuously removed from the liquid reaction solution, the net reaction (Eq. 1) becomes favorable (in the forward direction) according to Le Chatelier's principle. Therefore, it is preferable to remove at least one of the gaseous products as it is formed; it is especially preferable to remove both products ($H_2$ and $CO_2$) at the same rate that they are formed, to avoid accumulation and favor complete conversion of the polysaccharide.

More water consumed (a>7 in Eq. 1b) will not generate more hydrogen, but rather will tend to cause traditional glucan hydrolysis, producing shorter chains along with dissipation of energy into the solution. Polysaccharide chain-shortening substrate phosphorylation (Eq. 2) utilizes the energy stored in the glucosidic bonds of polysaccharides (15.5 kJ/mol glucosidic bond) to produce the activated phosphorylated monosaccharide (G-1-P) without ATP consumption. In essence, energy that is stored in polysaccharides is channeled to water molecules to break them up and release the energy in the form of hydrogen.

Polysaccharide hydrolysis can be minimized even with excess water present, by using a solution that is substantially free of hydrolytic enzymes (e.g., amylases for starch or cellulases for cellulose). Therefore, in preferred embodiments of the invention, the liquid solution does not contain a significant quantity of active hydrolytic enzymes. Any glycosidic bonds between two glycoside units contain chemical bond energy. Simple hydrolysis of glycosidic bonds for polysaccharides and oligosaccharides dissipates the bond energy of glycosidic bonds. In nature, phosphorylases can conserve the energy by substrate phosphorylation.

Phosphorylases are allosteric enzymes that catalyze the production of glucose-1-phosphate. More generally, phosphorylases are enzymes that catalyze the addition of a phosphate group from an inorganic phosphate to an acceptor. Phosphorylases include EC 2.4.1.1 (1,4-α-glucan phosphorylase, α-glucan phosphorylase, amylopectin phosphorylase, amylophosphorylase, glucan phosphorylase, glucosan phosphorylase, glycogen phosphorylase, maltodextrin phosphorylase); EC 2.4.1.8 (maltose phosphorylase); EC 2.4.1.20 (cellobiose phosphorylase); EC 2.4.1.49 (cellodextrin phosphorylase); and EC 2.4.1.7 (sucrose phosphorylase). Effective phosphorylases can also be selected from enzymes with at least 80% identity, preferably at least 90% identity, to the enzymes recited in this paragraph.

For substrates containing α-1,4-glucosidic bonds, such as starch, the phosphorylation reactions are as follows:

$(1,4\text{-}\alpha\text{-D-glucosyl})_{n} + Pi + H_2O \rightarrow (1,4\text{-}\alpha\text{-D-glucosyl})_{n-1} +$
G-1-P maltose+Pi+$H_2O$→glucose+G-1-P For substrates containing β-1,4-glucosidic bonds, such as cellulose, the phosphorylation reactions are as follows:

$(1,4\text{-}\beta\text{-D-glucosyl})_{n} + Pi + H_2O \rightarrow (1,4\text{-}\alpha\text{-D-glucosyl})_{n-1} +$
G-1-P cellobiose+Pi+$H_2O$→G-1-P+glucose After a series of phosphorolysis reactions mediated by phosphorylases, a large amount of G-1-P can be produced reversibly. The removal of G-1-P will lead to chain-shortening reactions.

Phosphoglucomutases are enzymes that create a glucose isomer by changing the site of the phosphate ion, converting between G-1-P and G-6-P. An example of a phosphoglucomutase is the enzyme characterized by EC 5.4.2.2, or an enzyme with at least 80% identity, preferably at least 90% identity, to such as enzyme.

Hydrogenases are enzymes that catalyze the reversible oxidation of molecular hydrogen ($H_2$). Hydrogenases play a vital role in anaerobic metabolism. Hydrogen uptake ($H_2$ oxidation) is coupled to the reduction of electron acceptors such as oxygen, nitrate, sulfate, carbon dioxide, and fumarate, whereas proton reduction ($H_2$ evolution) is essential in pyruvate fermentation and in the disposal of excess electrons. Hydrogenase can produce hydrogen gas from NADPH according to the following reaction:

$$NADPH + H^+ \rightarrow NADP^+ + H_2$$

An example of a hydrogenase is the enzyme characterized by EC 1.12.1.3, or an enzyme with at least 80% identity, preferably at least 90% identity, to such as enzyme. Some embodiments of the invention employ a hydrogenase isolated from a hyper-thermophilic archaebacterium *Pyrococcus furiosus* (Bryant and Adams, 1989; Ma and Adams, 1994; Ma et al., 1994; Pedroni et al., 1995; Ma et al., 2000). Although the NADPH reduction reaction is not driven spontaneously, the special *Pyrococcus furiosus* hydrogenase 1 can catalyze NADPH reduction to generate hydrogen in vitro.

The pentose-phosphate pathway consists of an oxidative phase, which converts G-6-P into ribulose-5-P, and a non-oxidative phase, which regenerates G-6-P from ribulose-6-P:

G-6-P+2 NADP$^+$+$H_2O$→ribulose-5-P+2 H$^+$+$CO_2$+2
NADPH ribulose-5-P-→5/6 G-6-P In general, selection of a plurality of enzymes that activate the pentose-phosphate pathway is within the skill of an ordinary artisan. One particular embodiment is discussed in Example 1 (see Table 1). Other embodiments employ similar enzymes, such as enzymes with at least 80%, preferably at least 90%, sequence identity to the pentose-phosphate pathway enzymes listed in Table 1 (EC numbers 1.1.1.49, 1.1.1.44, 5.3.1.6, 5.1.3.1, 2.2.1.1, 2.2.1.2, 5.3.1.1, 4.1.2.13, 3.1.3.11, and 5.3.1.9).

In some embodiments, enzymes are added directly into the aqueous solution of polysaccharides. The quantity of enzymes to add depends on the desired reaction temperature and residence time. In general there will be concentration of each particular enzyme above which no further enhancement in reaction rate occurs. The optimal quantity of enzyme will be dictated by overall economics.

The enzymes may be purified (but are not necessarily purified), and they can exist in the form of mixtures of enzymes or enzyme complexes with the desired functions. Enzymes can be added in the form of lysed cells which produced the enzymes in a previous fermentation process. In this case, there could also be cell fragments added to the reactor.

In some embodiments, inorganic phosphate (Pi) and coenzyme (NADPH) are continuously recycled in the system. That is, these substances are produced and consumed at equal rates. A small amount of inorganic phosphate can be added, if necessary, at the beginning of the process in order to initiate phosphorylation. Also, if necessary (due to side reactions or other reasons), additional Pi and/or NADPH can be added at any point within the process.

The pH of the solution is not regarded as particularly critical, but pH will impact the activity of each enzyme in a potentially different way. Also, it is noted that the reaction that generates $H_2$ in the pathway of the invention consumes protons, the concentration of which is controlled by the pH of the solution. A person of ordinary skill in the art can readily perform routine experimentation, given a specific selection of enzymes, to determine the system-optimum pH, or to determine a range of preferred pH values, with respect to $H_2$ yield or production rate. In other words, the process of the invention can comprise adjusting one or more parameters during the reaction to maintain a parameter or optimize a parameter. An illustrative range of preferred pH values for some embodiments is pH=2-12, more preferably 4-9, and most preferably a neutral pH, such as pH 6-8.

Temperature is not regarded as being critical to the present invention. Low to moderate temperatures are appropriate, especially when mesophilic enzymes are chosen. The process can generally be practiced conveniently at one or more temperatures from about 10° C. to about 100° C., preferably from about 25° C. to about 75° C. Each of the enzymes selected will have its own respective functions of activity versus temperature, and the overall optimum temperature will be a function of the specific enzymes chosen. One skilled in the art will recognize that temperatures outside the range of 10° C. to 100° C. could even be employed, such as when thermophilic or psychrophilic enzymes are selected. In some embodiments, no external energy is added, and the temperature will be a function of substrate concentrations, net heats of reactions, and heat losses in the system.

Pressure is also not critical to the present invention, but a skilled artisan will appreciate that the reaction pressure can impact the equilibrium distribution of species. A high pressure, such as several atmospheres, would tend to inhibit product gas evolution. Conversely, a low system pressure will tend to push the equilibrium towards products (hydrogen and carbon dioxide). For convenience, the reactions are preferably conducted at atmospheric pressure. The process could be conducted under a vacuum. Also, the process could be performed in the presence of gases other than those produced or consumed, such as air, nitrogen, helium, argon, and the like.

The process can be conducted in a batch reactor, a continuous reactor, or some combination of the two. A variety of means for agitation (mixing) can be employed, or a plug-flow reactor without internal mixing can be effective. Unconverted reactants (polysaccharides) can be recycled to the reactor inlet, as in known in the art.

With respect to Eq. 1b [$(glucan)_n + a\ H_2O \rightarrow (glucan)_{n-1} + b\ H_2 + c\ CO_2$], a person of ordinary skill in the art will understand that the process can be optimized, without undue experimentation, such that on an overall basis the coefficient a can be about 7, b can be about 12, and c can be about 6. In some embodiments, some side reactions do occur, reducing the yield to $H_2$. In other embodiments, the hydrogen-atom selectivity to $H_2$ is very high (at least about 90%) but the polysaccharide is not completely converted to products, resulting in lower yields. Economics sometimes dictate operating a process at something less than its highest attainable yield.

Optimization can also be carried out to improve the overall reaction rate and the stability of some or all of the enzymes. Such optimization can include, for example, enzyme component optimization via metabolic engineering and modeling; substitution of mesophilic enzymes by recombinant thermophilic or even hyperthermophilic enzymes; protein engineering to improve enzyme activity and/or selectivity; higher concentrations of enzymes and substrates; variation of process parameters such as pH and temperature; stabilization of enzymes through additives; enzyme immobilization; and development of minimal microorganisms to create an in vivo enzyme system that produces $H_2$. It is within the skill of a person of ordinary skill in the enzyme art to conduct such optimization, and the present invention is intended to include this type of experimentation. Statistical experimental design can be employed to explore global response surfaces and establish models of $H_2$ yield and rate versus process and enzyme factors as well as interaction effects.

As mentioned above, one aspect of the invention is a kit for performing the methods of the invention. In general, the kits are kits for generating and collecting hydrogen gas. The kits of the invention comprise some or all of the components necessary to practice one or more embodiment of the methods of the invention. Thus, a kit of the invention can comprise one or more of: (a) one or more enzymes with some phosphorylase activity; (b) one or more enzymes with some phosphoglucomutase activity; (c) one or more enzymes with some hydrogenase activity; (d) a container for combining a polysaccharide, water, and the enzymes from elements (a), (b), and (c); (e) means for heating the container to between about 10-100° C.; and (f) means for collecting or using some of the hydrogen gas that evolves from the container. The kits of the invention can also contain an enzyme composition as described above.

The enzymes, reagents, and additives (if desired) and other components can be provided in one or more suitable containers within the kit. The kit can comprise sufficient components to perform the method of the invention a single time or multiple times. Kits can be fabricated from any suitable material, such as plastic, glass, and metal.

Hydrogen has a number of possible uses. Molecular hydrogen is used for the production of ammonia; in petroleum refining, where $H_2$ is used throughout a typical refinery; in the chemical-synthesis industries, when conversion of a double carbon-carbon bond to a single C—C bond is desired, or of a triple carbon-carbon bond to a single or double bond; in the food industry for hydrogenation of vegetable oils; and in electronic-circuitry manufacture. Hydrogen is also used extensively today to make methanol, fertilizers, glass, refined metals, vitamins, cosmetics, soaps, lubricants, and cleaners. Further, pure hydrogen is an excellent fuel, both in traditional combustion engines as well as in fuel cells, and produces only water vapor when oxidized with oxygen. Liquid hydrogen can also be used as a fuel, such as in space vehicles.

The hydrogen produced by the process of the present invention can be separated from other substances (e.g., carbon dioxide) completely or partially, or it can be used in conjunction with the other substance(s). When it is desired to separate at least some of the $CO_2$ from the $H_2$, a variety of separation techniques are known. One such technique employs separation by molecular sieves. It would also be possible to separate $CO_2$ from $H_2$ using cryogenic distillation, for example.

An example of direct use of $H_2/CO_2$ mixtures is acetate production from $H_2$ and $CO_2$ using *Clostridium aceticum*, as is known in the art. Other means of biochemically, or chemically, converting $H_2/CO_2$ mixtures of various concentrations are also known.

EXAMPLE

The present invention will now be further characterized and described by reference to the following non-limiting example, which is intended to be purely exemplary of the invention, and is not to be understood as limiting the invention in any way. In summary, the following paragraphs will describe illustrative enzyme selections and experimental procedures that demonstrate one embodiment of the invention.

Example 1

Enzymatic Production of $H_2$ and $CO_2$ from Starch and Water

To exemplify the practical nature of the present methods, systems, and compositions, starch was converted to hydrogen and carbon dioxide in a process according to the present invention. Experiments were carried out in a continuous flow system with the moisture traps cooled with ice. All chemicals and enzymes were purchased from Sigma-Aldrich Co. (U.S.A.), unless otherwise noted. All enzymes and their catalysis reactions are listed in Table 1. The working volume of the custom reactor was 2 mL. The system was continuously purged with helium at a flow rate of 50 mL/min. The temperature of the jacketed reaction vessel was maintained at 30° C. with a Polyscience (Niles, Ill.) circulating water bath.

Figure 2:
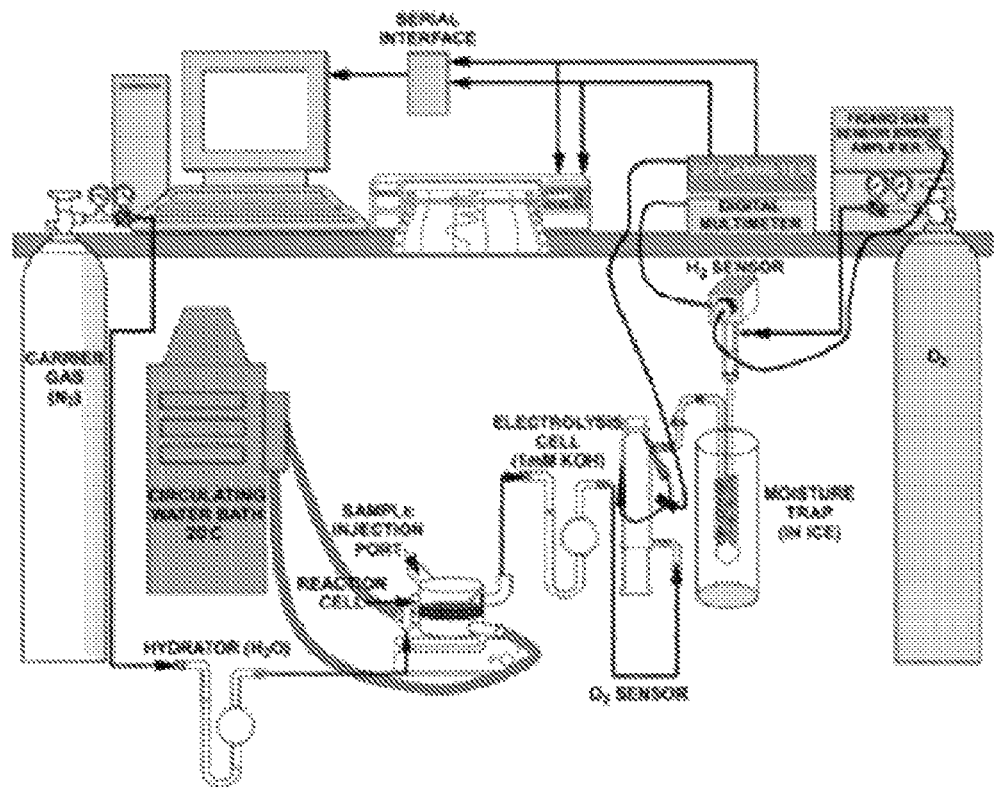
FIG. 2 shows a diagram depicting a system for generating and monitoring $H_2$ production through a process and system of the present invention.

FIG. 2 shows a diagram depicting the hydrogen cell system of the invention configured for monitoring $H_2$ with a sensor based on the Figaro TGS 822 and $O_2$ with a modified Hersh galvanic cell. The $CO_2$ analyzer (not shown) was attached between the reaction cell and the electrolysis cell. Oxygen as well as hydrogen and carbon dioxide were monitored in the gas stream. Hydrogen evolution was measured with a Figaro TGS 822 tin oxide sensor connected over a bridge amplifier to a Keithley Model 2000 multimeter (Keithley Instruments, Cleveland, Ohio). Oxygen concentration was monitored with a modified Hersh galvanic cell using 24% KOH as the electrolyte connected to a Keithley autoranging picoammeter. Carbon dioxide production was measured with a LI-COR $CO_2$ Analyzer Model LI-6252 connected to a Keithley 2000 multimeter. The multimeters and picoammeter were connected to a computer through IEEE 488 general-purpose interface boards. Electrolysis for calibration of hydrogen and oxygen by Faraday's law of electrochemical equivalence was carried out with a Keithley 220 programmable current source connected to an in-line electrolysis cell. Calibration for carbon dioxide was carried out with an analyzed gas mixture consisting of 735 ppm carbon dioxide and 1000 ppm oxygen in helium (Air Liquide America Corp., Houston, Tex.).

Data collection and analysis was carried out with ASYST 4.0 software (ASYST Technologies, Inc., Rochester, N.Y.). The integrated molar/molar yields of hydrogen ($Y_{H2}$) and carbon dioxide ($Y_{CO2}$) were calculated as $$Y_{H2} = \frac{\int y_{H2} dt}{12 * \Delta GE}$$

TABLE 1

Enzymes and Catalysis Reactions

| EC | Enzyme Name | Reaction | Origin | Units |
|---|---|---|---|---|
| 2.4.1.1 | glycogen phosphorylase | $(C_6H_{10}O_5)_n + P_i + H_2O \rightarrow (C_6H_{10}O_5)_{n-1}$ + glucose-1-P | rabbit muscle | 10 |
| 5.4.2.2 | phosphoglucomutase | G-1-P → G-6-P | rabbit muscle | 10 |
| 1.1.1.49 | glucose-6-phosphate dehydrogenase | G-6-P + $NADP^+$ → 6-phosphogluconate + NADPH | S. cerevisiae | 1 |
| 1.1.1.44 | 6-phosphogluconic dehydrogenase | 6-phosphogluconate + $H_2O$ + $NADP^+$ → ribulose-5-phosphate + NADPH + $CO_2$ | S. cerevisiae | 1 |
| 5.3.1.6 | ribose 5-phosphate isomerase | ribulose-5-phosphate → ribose-5-phosphate | spinach | 1 |
| 5.1.3.1 | ribulose-5-phosphate 3-epimerase | ribulose-5-phosphate → xylulose-5-phosphate | S. cerevisiae | 1 |
| 2.2.1.1 | transketolase | xylulose-5-phosphate + ribose-5-phosphate → sedoheptulose-7-phosphate + glyceraldehyde-3-phosphate | E. coli | 1 |
| 2.2.1.2 | transaldolase | sedoheptulose-7-phosphate + glyceraldehyde-3-phosphate → fructose-6-phosphate + erythrose-4-phosphate | S. cerevisiae | 1 |
| 5.3.1.1 | triose-phosphate isomerase | glyceraldehyde 3-phosphate → dihydroxyacetone phosphate | rabbit muscle | 1 |
| 4.1.2.13 | aldolase | glyceraldehyde 3-phosphate + dihydroxyacetone phosphate → fructose-1,6-bisphosphate | rabbit muscle | 1 |
| 3.1.3.11 | fructose-1,6-bisphosphate | fructose-1,6-bisphosphate + $H_2O$ → fructose-6-phosphate + Pi | E. coli | 1 |
| 5.3.1.9 | phosphoglucose isomerase | fructose 6-phosphate → glucose-6-P | S. cerevisiae | 1 |
| 1.12.1.3 | P. furiosus hydrogenase I | NADPH + $H^+$ → $NADP^+$ + $H_2$ | P. furiosus | ~70 |

-continued $$Y_{CO2} = \frac{\int r_{CO2} dt}{6 * \Delta GE}$$

in which $r_{H2}$ and $r_{CO2}$ are the volumetric production rates in mmole of $H_2$ or $C_{O2}$ per liter of reaction volume per hour, and $\Delta GE$ is the net consumption of glucose equivalents in mM.

Residual G-6-P can be measured using Sigma glucose HK kit. The mixtures were incubated at 35° C. for 5 minutes and the change in absorbance at 340 nm was determined. The residual starch, G-1-P, and G-6-P were hydrolyzed to glucose by addition of dilute $H_2SO_4$ and hydrolysis at 121° C. for 1 hour. The neutralized glucose solutions were measured by a glucose HK kit.

The solution contained 1 unit of each of the pentose phosphate cycle enzymes, approximately 70 units of *P. furiosus* hydrogenase, 10 units of α-glucan phosphorylase, 10 units of phosphoglucomutase, 4 mM phosphate, 0.5 mM thiamine pyrophosphate, 2 mM NADP+, 10 mM $MgCl_2$, and 0.5 mM $MnCl_2$ in 2.0 mL of 0.1 M HEPES buffer (pH 7.5). The experiment was conducted at about 30° C.

Figure 3:
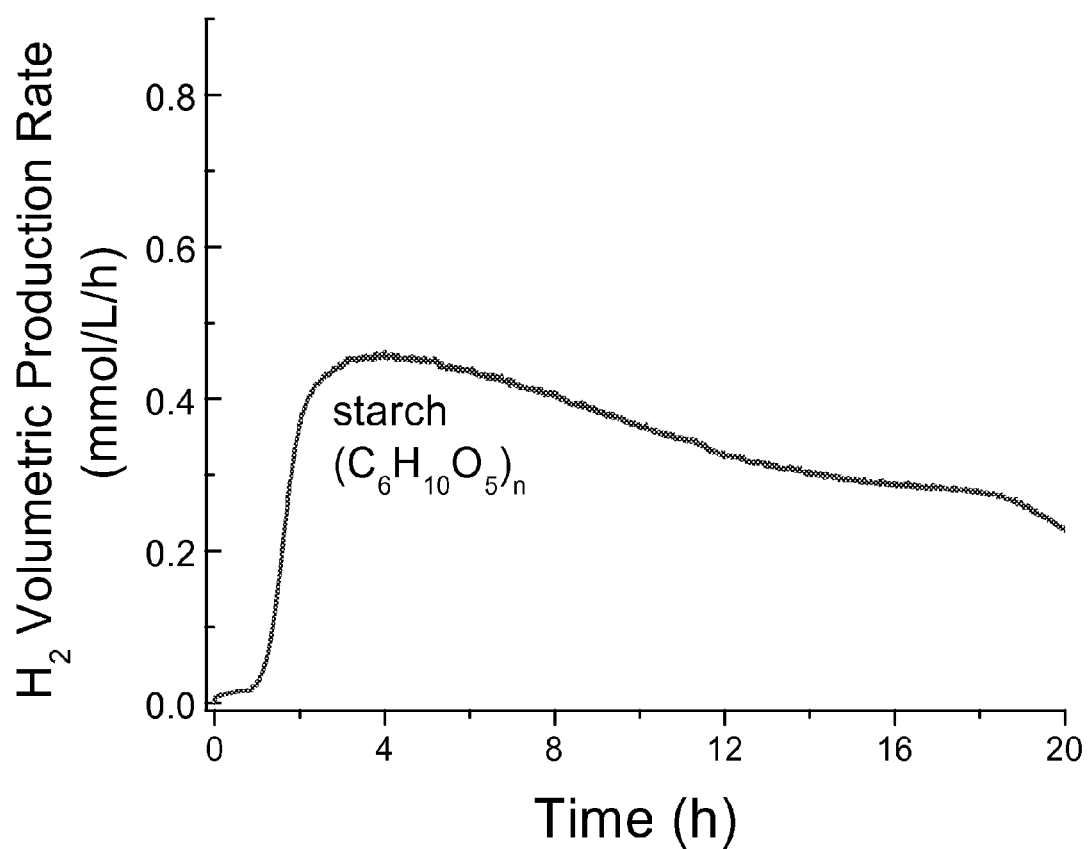
FIG. 3 shows the volumetric hydrogen production rate (mmol $H_2$/L/hr) from 2 mM starch in a process according to the present invention.

FIG. 3 shows the volumetric hydrogen production rate (mmol $H_2$/L/hr) from 2 mM starch. The integrated yields (mol/mol) of hydrogen and $CO_2$ were 5.19 $H_2$/glucan unit and 5.37 $CO_2$/glucan unit, respectively. The yields of hydrogen and $CO_2$ from starch were approximately 43% and 86% of theoretical yields. It is believed that the reduced hydrogen yield was due primarily to incomplete conversion and possibly accumulation of metabolites, such as NADPH.

Although illustrative embodiments and various modifications thereof have been described in detail herein, one skilled in the art will appreciate that the present application need not be limited to these precise embodiments and the described modifications, and that various changes and further modifications may be practiced without departing from the scope or spirit of the invention as defined in the appended claims. Other embodiments will be apparent to those of ordinary skill in the art, including embodiments that do not provide all of the features and advantages set forth herein.

REFERENCES

Alper J., *Science* 2003, 299:1686-1687.
Atkins P. W., *Physical Chemistry (fourth edition)*. New York: W. H. Freeman & Co.; 1990.
Atkins P. W. and De Paula J. *Elements of Physical Chemistry (4th edition)*. New York: W. H. Freeman & Co. (2005), 605-613.
Benemann et al., *Proc. Nat. Acad. Sci.* USA 70:2317, 1973.
Berg J. M. et al., *Biochemistry (fifth edition)*. New York: W. H. Freeman & Co.; 2002.
Bryant F. O. and Adams M. W. W, *J. Biol. Chem.* 1989, 264:5070-5079.
Cortright R. D. et al., *Nature* 2002, 418:964-967.
Deluga G. A. et al., *Science* 2004, 303:993-997.
Farrell A. E. et al., *Science* 2006, 311:506-508.
Hoffert M. I. et al., *Science* 2002, 298:981-987.
Huber G. W. et al., *Science* 2003, 300:2075-2077.
Klein and Betz, *Plant Physiol.* 61:953, 1978.
Lynd L. R. et al., *Microbiol. Mol. Biol. Rev.* 2002, 66:506-577.
Lynd L. R. et al., *Curr. Opin. Biotechnol.* 2005, 16:577-583.
Lynd L. R. et al., in *Cellulosome*. Edited by Kataeva IA: Nova Science Publishers, Inc.; 2006.
Ma K. and Adams M.W., *J. Bacteriol.* 1994, 176:6509-6517.
Ma K. et al., *FEMS Microbiol.* Lett. 1994, 122:245-250.
Ma K. et al., *J. Bacteriol.* 2000, 182:1864-1871.
Markov et al., *Advances in Biochemical Engineering and Biotechnology* 52:60, 1995.
Morris D., *J. Sci. Food Agric.* 86:1743-1746 (2006).
Muir M. etal., *J. Bacteriol.* 1985, 163:1237-1242.
Nelson D. L. and Cox M. M., *Lehninger Principles of Biochemistry (third edition)*. New York: Worth Publishers; 2000.
Pedroni P. et al., *Microbiol.* 1995, 141:449-458.
Rao et al., *Biochimie* 60:291, 1978.
Rosen and Krasna, *Photochem. Photobiol.* 31:259, 1980.
United States Department of Energy: "Basic Research Needs for the Hydrogen Economy" (2004) published at http://www.sc.doe.gov/bes/hydrogen.pdf.
Vatsala and Seshadri, *Proc. Indian Nat'l Sci. Acad.* B51:282, 1985.
Woodward J. et al., *Nat. Biotechnol.* 1996, 14:872-874.
Woodward J. et al., *Nature* 2000, 405:1014-1015.
Woodward J. et al., *Energy Fuels* 2000, 14:197-201.
Zhang Y.-H. P. and Lynd L. R., *Appl. Environ. Microbiol.* 2004, 70:1563-1569.
Zhang Y.-H. P. and Lynd L. R., *Proc. Natl. Acad. Sci. USA* 2005, 102:7321-7325.
Zhang Y.-H. P. and Lynd L. R., *Appl. Microbiol. Biotechnol.* 2006, 70:123-129.

The invention claimed is:

1. A process for producing hydrogen from a polysaccharide or oligosaccharide, said process comprising:
   using synthetic enzymatic pathway(s) for:
   reducing the number of glucan units of the polysaccharide by converting at least one glucan unit to glucose-6-phosphate;
   oxidizing the glucose-6-phosphate and oxidized coenzyme $NADP^+$ or its analog to 12 moles reduced coenzyme NADPH or reduced analog and 6 moles $CO_2$; and
   converting the 12 moles reduced coenzyme NADPH or reduced analog to 12 moles $H_2$ and 12 moles oxidized coenzyme $NADP^+$ or oxidized analog;
   wherein the process uses a single reaction vessel or several cascade reactors;
   and wherein an $H_2$ yield of 48% of theoretical yield up to 100% of theoretical yield is obtained from conversion of each glucan unit.

2. The process of claim 1, wherein the polysaccharide comprises starch, cellulose, or glycogen and the oligosaccharide comprises sucrose, cellobiose, lactose, maltose, cellodextrin, or maltodextrin.

3. The process of claim 1, wherein the polysaccharide comprises cellulose.

4. The process of claim 1, wherein the polysaccharide comprises hemicellulose.

5. The process of claim 1, wherein the polysaccharide is not starch or cellulose.

6. The process of claim 1, further comprising at least partially separating the hydrogen from carbon dioxide produced by the process.

7. The process of claim 6, further comprising feeding at least some of the hydrogen into a fuel cell.

8. The process of claim 1, further comprising generating electricity from the hydrogen.

9. The process of claim 1, wherein the maximum rate of hydrogen production is at least 0.4 mmol/L/hr.

10. The process of claim 1, wherein the synthetic enzymatic pathway(s) comprises:

(a) providing a mixture comprising a polysaccharide or oligosaccharide with phosphate and water;
(b) providing one or more enzymes with phosphorylase activity;
(c) phosphorylating at least some of the polysaccharide or oligosaccharide to produce glucose-1-phosphate and a shortened polysaccharide or oligosaccharide;
(d) providing one or more enzymes with phosphoglucomutase activity;
(e) isomerizing at least some of the glucose-1-phosphate produced in step (c) into glucose-6-phosphate;
(f) providing a plurality of enzymes effective to catalyze the steps of the pentose phosphate pathway for generating the reduced coenzyme NADPH or reduced analog from the oxidized coenzyme $NADP^+$ or oxidized analog;
(g) providing one or more enzymes with some hydrogenase activity for producing hydrogen from the reduced coenzyme NADPH or reduced analog; and
(h) forming hydrogen from at least some of the glucose-6-phosphate produced in step (e).

11. The process of claim 1, wherein the enzymatic pathway is implemented in a cell-free enzyme mixture.

12. The process of claim 1, wherein the enzymatic pathway is implemented by way of one or more living microorganisms.

13. The process of claim 1, wherein the yield of hydrogen is 48% of theoretical yield up to 99.99% of theoretical yield.

14. The process of claim 13, wherein the yield of hydrogen is at least 10 moles of hydrogen per mole of anhydroglucose units contained in the starting polysaccharide.

15. A process for producing hydrogen from a polysaccharide or oligosaccharide, said process comprising:
using synthetic enzymatic pathway(s) for:
reducing the number of glucan units of the polysaccharide by converting at least one glucan unit to glucose-6-phosphate;
oxidizing the glucose-6-phosphate and oxidized coenzyme $NADP^+$ or its analog to 12 moles reduced coenzyme NADPH or reduced analog and 6 moles $CO_2$; and
converting the 12 moles reduced coenzyme NADPH or reduced analog to 12 moles $H_2$ and 12 moles oxidized coenzyme $NADP^+$ or oxidized analog;
wherein the process uses a single reaction vessel or several cascade reactors;
and wherein an $H_2$ yield is obtained of at least 10 moles of hydrogen per mole of anhydroglucose units contained in the starting polysaccharide.

16. The process of claim 15, wherein the polysaccharide comprises starch, cellulose, or glycogen and the oligosaccharide comprises sucrose, cellobiose, lactose, maltose, cellodextrin, or maltodextrin.

17. The process of claim 15, wherein the polysaccharide comprises cellulose.

18. The process of claim 15, wherein the polysaccharide comprises hemicellulose.

19. The process of claim 15, wherein the polysaccharide is not starch or cellulose.

20. The process of claim 15, further comprising at least partially separating the hydrogen from carbon dioxide produced by the process.

* * * * *

UNITED STATES PATENT AND TRADEMARK OFFICE
CERTIFICATE OF CORRECTION

PATENT NO.       : 8,211,681 B2                          Page 1 of 1
APPLICATION NO.  : 11/747496
DATED            : July 3, 2012
INVENTOR(S)      : Yi-Heng Percival Zhang et al.

It is certified that error appears in the above-identified patent and that said Letters Patent is hereby corrected as shown below:

Title Page,
Item [73], delete the Assignee, and substitute the following:

-- (73)   Assignees: Virginia Tech Intellectual Properties, Inc., Blacksburg, VA (US);
                    UT-Battelle, LLC, Oak Ridge, TN (US) --

Signed and Sealed this
Twenty-third Day of October, 2012

David J. Kappos
*Director of the United States Patent and Trademark Office*